United States Patent [19]

Hibbs et al.

[11] Patent Number: 5,300,032

[45] Date of Patent: Apr. 5, 1994

[54] CATHETER INTRODUCER WITH FLEXIBLE TIP

[75] Inventors: Lee Hibbs, St. Louis, Mo.; Yue-teh Jang, Houston, Tex.; Vern Liebmann, Sugar Land, Tex.; Dennis Spinks, Angleton, Tex.

[73] Assignee: Mallinckrodt Medical, Inc., St. Louis, Mo.

[21] Appl. No.: 536,851

[22] Filed: Jun. 12, 1990

Related U.S. Application Data

[63] Continuation of Ser. No. 244,290, Sep. 15, 1988, Pat. No. 4,950,257.

[51] Int. Cl.⁵ .............................................. A61M 5/178
[52] U.S. Cl. ...................................... 604/164; 604/264; 604/265; 604/280
[58] Field of Search ............... 604/265, 264, 280-283, 604/158-170, 93; 128/658

[56] References Cited

U.S. PATENT DOCUMENTS

| | | |
|---|---|---|
| 4,100,309 | 7/1978 | Micklaus et al. . |
| 4,119,095 | 10/1978 | Micklus et al. .................... 128/844 |
| 4,563,181 | 1/1986 | Wijayarathna et al. . |
| 4,569,347 | 2/1986 | Frisbie et al. ...................... 604/171 |
| 4,588,398 | 5/1986 | Dougherty et al. ................ 604/265 |
| 4,610,655 | 9/1986 | Matsumoto et al. . |
| 4,610,674 | 9/1986 | Suzuki et al. . |
| 4,629,450 | 12/1986 | Suzuki et al. ...................... 604/164 |
| 4,636,346 | 1/1987 | Gold et al. ......................... 604/280 |
| 4,668,225 | 5/1987 | Russo et al. ....................... 604/280 |
| 4,950,257 | 8/1990 | Hibbs et al. . |

FOREIGN PATENT DOCUMENTS 093093 11/1983 European Pat. Off. .
144629 6/1985 European Pat. Off. .

OTHER PUBLICATIONS

Donald H. Lorenz, The Use of Hydromer Coatings on Medical Devices, pp. 1-7, Oct. 7, 1984.
Argon, "Introducer Kits", by Squibb Company.
Universal Medical Instrument Corp., "CATH SEAL ® Percutaneous Catheter Introducer System".
USCI, "Angiography Percutaneous Catheter Introducers".

*Primary Examiner*—C. Fred Rosenbaum
*Assistant Examiner*—Michael Rafa
*Attorney, Agent, or Firm*—Rothwell, Figg, Ernst & Kurz

[57] ABSTRACT

A catheter introducer has a tubular sheath with a relatively rigid tubular body and a soft flexible tubular tip for reducing sheath buckling tendencies.

6 Claims, 2 Drawing Sheets

CATHETER INTRODUCER WITH FLEXIBLE TIP

This is a continuation of application Ser. No. 07/244,290, filed Sep. 15, 1988, now U.S. Pat. No. 4,950,257.

BACKGROUND

1. Field of the Invention

The invention relates to catheter introducers or sheaths which are inserted through the skin into a blood vessel or other body cavity to enable easy insertion, placement and withdrawal of a catheter without perforation or excess trauma to the blood vessel or cavity wall.

2. Description of the Prior Art

Prior art introducers for blood vessels generally include a thin wall tube, commonly known as a sheath, which has its distal end inserted through the skin into the blood vessel. A hub or valve housing is attached to the proximal end of the tube and contains a valve and seal structure through which a catheter is inserted into the tube and then into the blood vessel. The catheter is advanced, by using longitudinal and rotative motion, in a sometimes tortuous path through various blood vessels to place the catheter tip in the desired position. The thin wall tube, which extends for a short distance in the lumen of the blood vessel, protects the blood vessel adjacent the entrance site against perforation and abrasion from the catheter during its insertion and placement, and together with the valve and seal structure, maintains a fluid-tight relationship with the blood vessel to prevent leakage.

To insert the introducer into the blood vessel, a Seldinger type needle is often used to pierce a path through the skin and underlying tissue into the blood vessel. A guide wire is inserted through the needle and into the blood vessel after which the needle is withdrawn over the guide wire. Then an assembly of the introducer with a tubular dilator extending through the lumen of the introducer is slipped over the guide wire with the tips of the dilator and introducer being forced into the blood vessel. The dilator and guide wire are removed leaving the introducer in position to receive and guide the catheter into the blood vessel. The introducer may also include a side port downstream from the valve and seal in the housing for allowing withdrawal or infusion of fluids, such as heparin, through the introducer while the catheter is in place.

Introducer tubes must have sufficient strength, rigidity, and lubricity to enable insertion of the introducer tube into the blood vessel and to provide a low resistance pathway for a catheter being threaded into the blood vessel. Generally these requirements for strength, rigidity, and lubricity could only be met with tubes formed from polytetrafluoroethylene or high density polyethylene.

Due to the relative stiffness of the sheath, and the edge sharpness resulting from the thin wall, there is a tendency for the sheath to abrade or perforate the vessel wall either during insertion or patient movement. Also introducer tube tips have been known to split or fracture during the insertion process as a result of forces created upon being forced into body tissue.

Another problem associated with prior art introducers is the tendency for the thin walled tube to buckle or fold during insertion. The rigidity of the tube sometimes causes the wire guide to bend or fold or the tip to snag on tissue to thus lead to a buildup of forces in the tube to cause the buckling or folding of the tube commonly near to the junction of the housing with the tube. These folds have been known to impede catheter introduction or to restrict fluid delivery. Also these folds can promote thrombus formation due to blood retention at the fold site.

U.S. Pat. No 4,610,674 discloses a catheter introducer having a reinforcing coil body fitted in a connecting portion of the hub and extending axially of the sheath from the connection portion toward the distal end of the sheath beyond the connection portion. The reinforcing coil prevents folding of the sheath at the junction of the sheath and hub.

Soft tips are commonly employed on catheters in order to avoid injury to blood vessels. For example, U.S. Pat. No. 4,563,181 discloses a tubular body portion of a catheter formed from nylon-11 with a soft tubular tip formed from a blend of nylon-11 and an ester linked polyether-polyamide copolymer commonly known as polyether block amide (PEBA) fused onto the distal end of the tubular body portion. The tips of catheters are made soft so that they avoid penetration through blood vessel walls.

The use of a coating of hydrogel material including polyvinylpyrrolidone-polyurethane interpolymer on catheters to reduce insertion friction and to reduce thrombogenicity is disclosed in U.S. Pat. No. 4,100,309 to Micklus et al. The disclosed hydrogel material has been successfully coated on polyurethane catheters and silicone wound drains. It has been disclosed that the hydrogel material will also adhere to polyvinyl chloride, polymethyl methacrylate, polycarbonate, polyethylene terephthalate, polybutylene terephthalate, polytetramethylene terephthalate, latex rubber and polyisoprene. The hydrogel material can be applied to fluorocarbons and polyolefins which have been subjected to surface preparation to assure adequate wetting and bonding of the coating. The coating, when exposed to water, swells and develops a low coefficient of friction.

SUMMARY OF THE INVENTION

The invention is summarized in a catheter introducer having a body portion formed from a thin-walled flexible tube with an attached soft flexible tip for extending into a body cavity or blood vessel to guide a catheter during insertion and placement of the catheter in the cavity or vessel. A valve and seal structure is attached to a proximal end of the body portion for closing the proximal end of the body portion when the catheter is withdrawn and for forming a seal at the proximal end during insertion and placement of the catheter to prevent leakage. The tip portion is formed from a polymer material rendering the tip portion substantially more flexible than the tube forming the body portion.

An object of the invention is to construct a new and improved catheter introducer with reduced tendency to split or buckle or to abrade or traumatize a vessel wall during use.

An advantage of the invention is that a soft tip on an introducer does not impede forcing of the introducer into a blood vessel.

One feature of the invention is that a soft tip on an introducer, in addition to reducing abrasion and perforation of a vessel wall, enables the tip portion to bend through a substantially greater curvature without buckling.

Another feature of the invention is that a soft tip on an introducer provides a region of greater elasticity on the tip portion of the introducer to enable the tip to absorb stress during insertion of an introducer into a blood vessel or during insertion and placement of a catheter to avoid splitting of the tip.

A further feature of the invention is that a soft flexible tip readily follows the bending of a guide wire during insertion to avoid snagging on tissue during insertion to thus reduce tissue trauma, and buckling or bending tendencies.

Still another feature of the invention is the employment of a highly lubricious coating on the internal and/or external surfaces of the sheath portion of an introducer for reducing strength and rigidity requirements of the introducer to withstand forces during insertion in a blood vessel and during placement of a catheter.

Other objects, advantages, and features will be apparent from the following description of the preferred embodiments taken in conjunction with the accompanying drawings.

DESCRIPTION OF THE PREFERRED EMBODIMENTS

Figure 1:
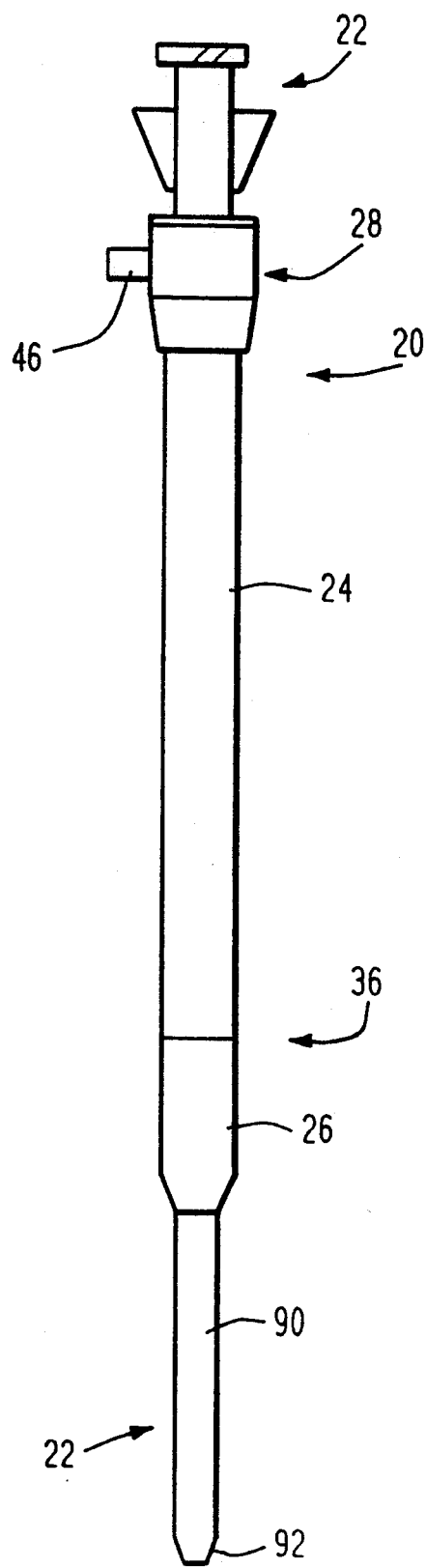
FIG. 1 is a side view, with a portion broken away, of a catheter introducer system in accordance with the invention.
Figure 2:
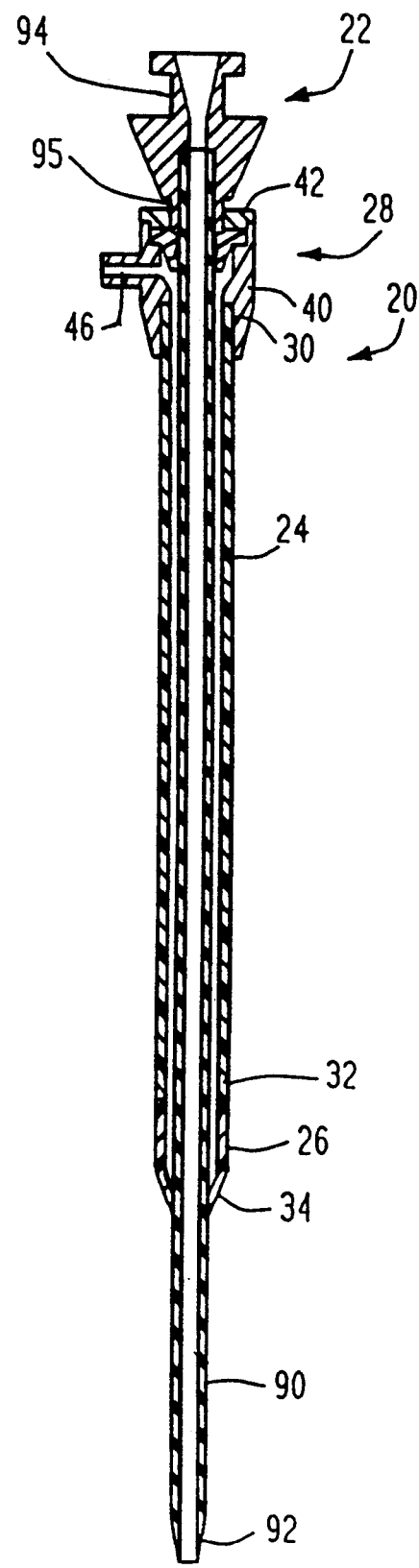
FIG. 2 is a sectional view of an introducer and dilator assembly of the system of FIG. 1.
Figure 11:
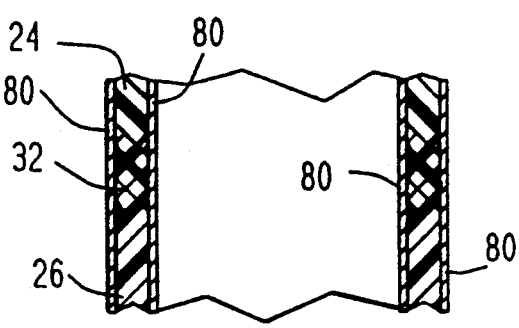
FIG. 11 is an enlarged sectional view of a tube portion of the introducer of FIGS. 1 and 2.

As shown in FIGS. 1 and 2, one embodiment of the invention is an introducer system including an introducer, indicated generally at 20, and a dilator, indicated generally at 22, for insertion over a guide wire (not shown) through tissue into a blood vessel. The introducer 20 includes a flexible tubular body portion 24, a short soft tubular tip portion 26 attached to the distal end of the body portion 24, and a valve and seal structure indicated generally at 28 attached to the proximal end 30 of the body 24. The body 24 and tip 26 together form a sheath, indicated generally at 36, which, after removal of the guide wire and dilator, provides a sealed and protected pathway for a catheter (not shown) through the layers of tissue at the wound or entrance site into the blood vessel. A lubricious anti-thrombogenic hydrogel coating 80, FIG. 11, is provided on the interior surfaces of the introducer and on the exterior surfaces of the sheath 36.

Surprisingly, the short soft tip 26 does not interfere with forcing of the distal end of the introducer through tissue into a blood vessel or body cavity, but rather the greater elasticity and flexibility of the soft tip enables the tip to bend more sharply without snagging, buckling or folding while following the curvature of the guide wire through the tissue. Lubricity of the hydrogel coating 80 on the external surface of the tip 26 assists forcing of the tip 26 through the tissue. The soft tip 26 produces less trauma to tissue during insertion, and to the blood vessel wall during catheter placement or patient movement.

The tubular body 24 is formed from a polymeric material, such as polyamide, polyethylene, polypropylene, or copolymers thereof. The tubular tip 26 is formed from a similar attachable polymeric material but of a softer and more flexible compound thereof. Particularly preferred polymeric materials for the body 24 and the tip 26 are nylon and ester linked polyether-polyamide copolymer or blends thereof in proportions selected to produce desired properties for the body 24 and the tip 26. The preferred nylon is unplasticized nylon-11. The ester linked polyether-polyamide co-polymer material is commonly known as polyether block amide (PEBA). This copolymer is chemically represented as:

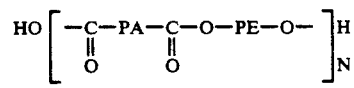

where PA is a polyamide and PE is a polyether and where N is an integer greater than 1 representing the number of blocks of copolymer molecular units within the molecular formula of the copolymer. The copolymer is commercially available in a variety of molecular weights or formulations which are designated by their physical properties such as Shore hardness, tensile strength, and elongation. Copolymers of polyamide and polyether having a Shore hardness in the range from 25D to 70D are generally suitable for use in blends forming the body 24 and/or tip 26. Preferred PEBA copolymers for blending with nylon-11 to form the body 24 have a Shore hardness in the range from 40D to 65D, and preferred PEBA copolymers for blending with nylon-11 to form the flexible tip 26 have a Shore hardness in the range from 30D to 50D.

The polymer materials forming the body 24 and the tip 26 of the introducer can include from 0% to 100% by weight PEBA copolymer and from 100% to 0% by weight nylon-11. For the body 24, the nylon-PEBA blend preferably includes from 0 to 50 percent by weight PEBA copolymer, and for the soft flexible tip 26, the nylon-PEBA blend preferably includes from 50 to 100 percent by weight PEBA.

The Shore hardness of the PEBA and the percentages of PEBA and nylon-11 in the body portion 24 are selected such that the body portion 24 can be formed with a thin wall which has sufficient rigidity and columnar strength to withstand the forces applied by a physician to drive the sheath through tissue stretched by the dilator around an opening through which a guide wire extends. The Shore hardness of the PEBA and the percentages of PEBA and nylon-11 in the tip portion 26 are selected in conjunction with the length of the tip portion 26 so that the tip 26 is substantially softer and more flexible than the body portion 24 so as to substantially reduce the tendency to abrade or perforate the wall of the blood vessel and to permit the tip portion to flex and closely follow a curvature of a guide wire to prevent snagging, buckling, or splitting of the tip without substantially interfering with capability of the tip to be forced through tissue during insertion into a blood vessel. For a short tip portion 26 having a length from 0.5 inches (1.2 cm) to 1 inch (2.5 cm), the tip 26 has a hardness, as measured by Shore hardness, which is from 25 to 75 percent of the hardness of the body portion 24. Shorter tip portions can be softer while longer tip portions require more rigidity and columnar strength.

In one specific example of an introducer, the body portion 24 is formed from a blend of nylon-11 and PEBA having a Shore hardness of 55D wherein nylon-11 is 60 percent by weight of the mixture and PEBA is 40 percent by weight of the mixture. The tip portion 24 has a length of 0.75 inches (1.9 cm) and is formed from a blend of nylon-11 and PEBA having a Shore hardness of 40D wherein nylon-11 is 35 percent by weight of the mixture and PEBA is 65 percent by weight of the mixture.

Typically the sheath 36 has a wall thickness in the range from 0.004 to 0.006 inches (0.10 to 0.15 mm). For an introducer designed to accommodate an 8 French (2.67 mm external diameter) catheter, the sheath 36 has an external diameter of about 0.137 inches (3.48 mm) and the tapered distal end 34 has an internal diameter of about 0.109 inches (2.77 mm). For introducers accommodating smaller catheters down to 4 French (1.33 mm) the diameter of the sheath 36 is generally about 0.8 mm larger than the diameter of the catheter and the opening 34 is generally about 0.1 mm larger than the diameter of the catheter. A typical introducer has a total shield length of about 4.75 inches (12 cm).

The tip 26 is thermally or chemically attached to the body 24. Region 32 is the region of bond and generally includes a varying mixture resulting from chemical or thermal fusion of the materials of the body 24 and tip 26. The bond is formed in a manner to produce continuous smooth inner and outer walls from the body 24 to the tip 26. The extreme distal end 34 of the tip 26 is tapered so that the end 34 provides a gradual or smooth increase in diameter from the dilator tube to enable easy insertion through tissue.

Figure 3:
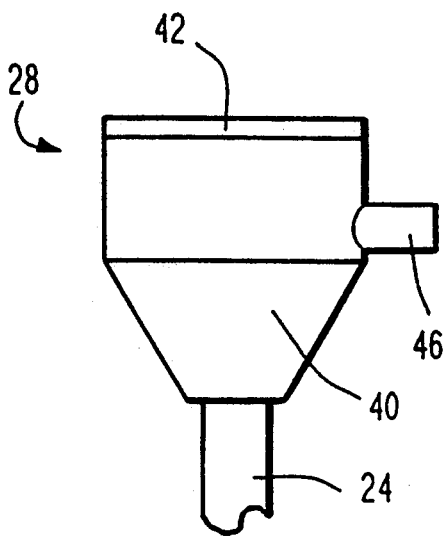
FIG. 3 is an enlarged side view of a valve and seal unit of the introducer of FIGS. 1 and 2.
Figure 4:
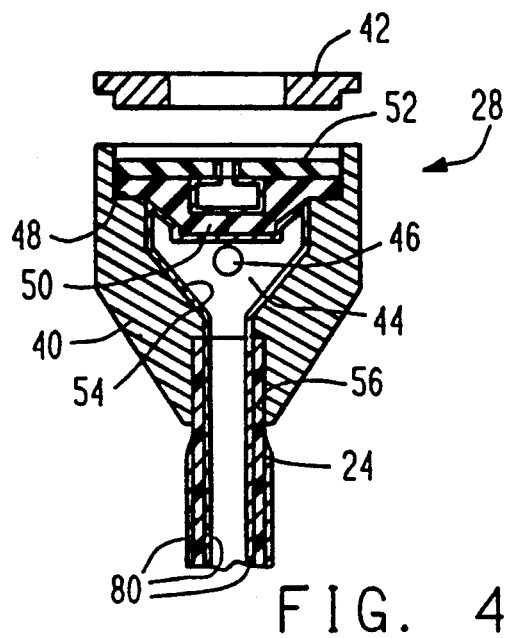
FIG. 4 is a sectional view, with a portion exploded, of the valve and seal unit of FIG. 3.
Figure 5:
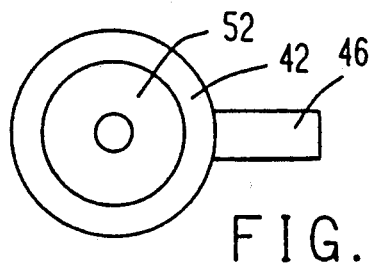
FIG. 5 is a top view of the valve and seal unit of FIGS. 3 and 4.
Figure 6:
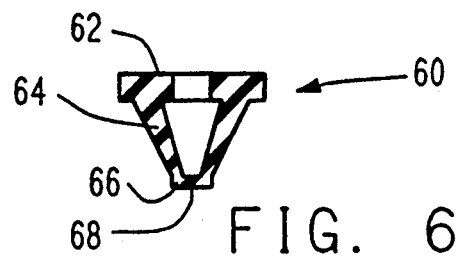
FIG. 6 is a sectional view of a valve and seal for employment in the unit of FIGS. 3 and 4.

As illustrated in FIGS. 3 and 4, the valve and seal structure 28 has a generally tubular housing 40 with a seal and valve retaining cap or ring 42 wherein the housing 40 and ring 42 are formed from polyamide, polyethylene, polystyrene, or other suitable resin. The housing 40 defines a cavity or chamber 44 with a port 46 for introducing or withdrawing fluid through the introducer sheath 36. Retained between the ring 42 and an annular rearward facing ledge 48 of the housing 40 at the rear end of the chamber 44 are a valve 50 for closing the rear end of the chamber 44 when a catheter is not present and a seal 52 for sealing the rear of the chamber with the external diameter of a catheter extending through seal and valve arrangement. The forward end 54 of the chamber 44 is tapered down to the internal diameter of the tubular body 24 to facilitate introduction of the catheter into the tube 24 which is secured in a forward enlarged portion 56 of a front opening of the chamber 44 in the housing 40. The attachment of the tube 24 to the housing 40 and the attachment of the holding ring 42 to the housing 40 are accomplished by ultrasonic welding, RF welding, solvent bonding, adhesive bonding, insert molding, or any other conventional attaching technique. The size of the chamber 44 and the spacing of the port 46, valve 50, and termination point of the tube 24 is such that minimal spacing is achieved between the valve 50 and the forward end of the chamber 44 without causing obstruction of the port 46 from expansion of the valve 50 by the presence of a catheter. The spacing between the valve 50 and the narrow end of the conical wall 54 is sufficiently short such that catheters with preformed acute angles being inserted into the catheter are prevented from reforming to their preformed curvature from the substantially straightened condition in which they are inserted into the introducer. Also the forward exit point of the valve 50, for a catheter being inserted into the introducer, is even with the port 46 so that the tip of the catheter will not engage the port opening which otherwise could cause folding or obstruction of the catheter being inserted.

Figure 7:
FIG. 7 is a top view of the valve and seal of FIG. 6.
Figure 8:
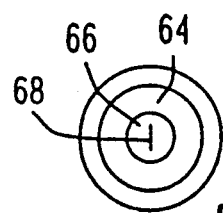
FIG. 8 is a bottom view of the valve and seal of FIG. 6.
Figure 9:
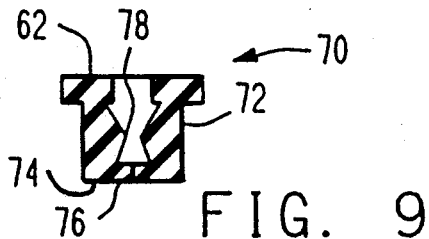
FIG. 9 is a sectional view of a modified valve and seal for employment in the unit of FIGS. 3 and 4.
Figure 10:
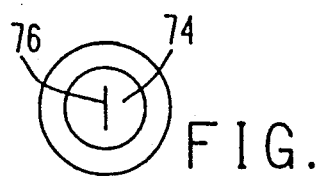
FIG. 10 is a bottom view of the modification of FIG. 9.

As an alternative to the separate seal and valve structures of FIG. 4, a unitary valve and seal structure 60, shown in FIGS. 7, 8 and 9, may be used in the housing 40. The unitary valve and seal structure 60 has a rear disc-like seal portion 62, and a conical valve portion 64 which terminates in a forward disc portion 66 with a slit 68. A further alternative unitary valve and seal structure 70, shown in FIGS. 9 and 10, employs a tubular or cylindrical valve portion 72 with a forward end wall 74 in which the valve slit 76 is formed. The tubular portion 72 has a necked down central portion 78 which, with the seal portion 62, forms a double seal arrangement. The valve 50, the seal 52, and the unitary valve and seal structures 60 and 70 are formed from an elastomeric material, such as a silicone polymer, permits easy insertion of a catheter but forms an effective valve and seal preventing leakage of fluids from the introducer.

The lubricious hydrophilic coating 80, FIG. 11, is provided on both inner and outer surfaces of the sheath 36, the internal surface of the housing 40, and the surfaces of the valve and seal structures 50, 52, 60 and 70. The lubricious hydrophilic coating 80 is a biocompatible hydrogel material such as a copolymer of polyurethane and polyvinylpyrrolidone or cross-linked copolymer of polyethylene oxide and polyhydroxyethyl methacrylate. The hydrogel material is commercially available in solutions having from 1 to 3 parts by weight polyvinylpyrrolidone to 1 part polyurethane. Preferred hydrogel materials for catheters have 2 to 3 parts by weight polyvinylpyrrolidone to 1 part polyurethane. Copolymers of polyurethane and polyvinylpyrrolidone have the advantage of being highly anti-thrombogenic. The hydrogel copolymer is dissolved in a mixture of liquid organic solvents and is applied by flushing, dipping, or spraying the solution on the parts or portions of the introducer to be coated to form a thin layer. The liquid layer is then dried and cured in an oven forming a final layer 80 which is about 1 mil (0.025 mm) thick. The layer 80, when wetted with water such as during flushing saline solution before placing in use, swells and becomes slippery.

The dilator 22 is a conventional type dilator with a tube 90 having a tapered leading end 92 and a luer fitting member 94 attached to the proximal end. The tube 90 is formed from any suitable polymer, e.g. polyamide, polyethylene, polypropylene, or copolymers thereof, and the member 94 is formed from any suitable polymer, e.g. polyamide, polyethylene, polystyrene, or other suitable resin. The fitting member 94 has a forward extending portion 95 which releasably locks with the housing cap 42, such as by snap fitting or wedge fitting into the rear opening of the housing cap so as to maintain the dilator position in the introducer during insertion into a blood vessel.

Since many modifications, variations, and changes in detail may be made to the above described embodiments, it is intended that all matter described in the foregoing description and shown in the accompanying drawings be interpreted as only illustrative not as limiting to the scope and spirit of the invention as defined in the following claims.

What is claimed is:

1. A catheter introducer comprising
    a thin-walled flexible tube for being forced through tissue stretched by a dilator around an opening through which a guide wire extends, so as to extend the tube into a body cavity or blood vessel, the tube being sized to receive a catheter therein and permit the catheter to pass therethrough, the tube having an interior surface for guiding the catheter during insertion and placement of the catheter in the cavity or vessel,
    said tube having a body portion and a distal tip portion, wherein a substantial part of said distal tip portion has an outer diameter equal to that of the body portion,
    said tube having sufficient rigidity and columnar strength to withstand forces applied by a physician to drive the tube through the dilator-stretched tissue,
    said tube forming the tip portion being substantially more flexible than the tube forming the body portion, and
    a coating of lubricous hydrogel covering the interior catheter-guiding surface of the tube for contacting the catheter so as to promote ease of catheter insertion.

2. A catheter introducer as claimed in claim 1 wherein the flexible tube has a coating of lubricious hydrogel on the exterior surface to render insertion through tissue easier.

3. A catheter introducer as claimed in claim 1 wherein the hydrogel is a copolymer of polyurethane and polyvinylpyrrolidone having from 1 to 3 parts by weight polyvinylpyrrolidone to 1 part polyurethane.

4. A catheter introducer as claimed in claim 2 wherein the hydrogel on both the interior and exterior surface is a copolymer of polyurethane and polyvinylpyrrolidone having from 1 to 3 parts by weight polyvinylpyrrolidone to 1 part polyurethane.

5. A catheter introducer comprising
    a thin-walled flexible tube for being forced through tissue stretched by a dilator around an opening through which a guide wire extends, so as to extend the tube into a body cavity or blood vessel, the tube being sized to receive a catheter therein and permit the catheter to pass therethrough, the tube having an interior surface for guiding the catheter during insertion and placement of the catheter in the cavity or vessel,
    said tube having a body portion and a distal tip portion, wherein a substantial part of said distal tip portion has an outer diameter equal to that of the body portion,
    said tube having sufficient rigidity and columnar strength to withstand forces applied by a physician to drive the tube through the dilator-stretched tissue,
    said tube forming the tip portion being substantially more flexible than the tube forming the body portion, and
    a coating of lubricous hydrogel on the exterior surface to render insertion through tissue easier.

6. A catheter introducer as claimed in claim 5 wherein the hydrogel is a copolymer of polyurethane and polyvinylpyrrolidone having from 1 to 3 parts by weight polyvinylpyrrolidone to 1 part polyurethane.

* * * * *